United States Patent [19]

Moest

[11] Patent Number: 5,270,055
[45] Date of Patent: Dec. 14, 1993

[54] SOLID PHARMACEUTICAL SUSTAINED-RELEASE FORM

[75] Inventor: Thomas Moest, Moorrege, Fed. Rep. of Germany

[73] Assignee: Nordmark Arzneimittel GmbH, Uetersen, Fed. Rep. of Germany

[21] Appl. No.: 426,018

[22] Filed: Oct. 24, 1989

[30] Foreign Application Priority Data

Nov. 10, 1988 [DE] Fed. Rep. of Germany ....... 3838094

[51] Int. Cl.$^5$ .................... A61K 9/24; A61K 9/36; A61K 9/42
[52] U.S. Cl. ................................. 424/476; 424/472; 424/480; 424/482; 424/475; 424/498
[58] Field of Search ............... 424/472, 476, 480, 461, 424/495, 498

[56] References Cited

U.S. PATENT DOCUMENTS

| | | | |
|---|---|---|---|
| 3,939,259 | 2/1976 | Pescetti | 424/490 |
| 4,289,795 | 9/1981 | Bogentoft et al. | 424/468 |
| 4,716,041 | 12/1987 | Kjornaes et al. | 424/468 |
| 4,723,034 | 2/1988 | Schimer et al. | 560/60 |
| 4,755,387 | 7/1988 | Tzeghai et al. | 424/480 |
| 4,822,908 | 4/1989 | Karbach et al. | 560/60 |

FOREIGN PATENT DOCUMENTS

| | | |
|---|---|---|
| 0178826 | 4/1986 | European Pat. Off. |
| 0242081 | 10/1987 | European Pat. Off. |
| 0244077 | 11/1987 | European Pat. Off. |
| 0260794 | 3/1988 | European Pat. Off. |
| 0299694 | 1/1989 | European Pat. Off. |
| 1146621 | 3/1969 | United Kingdom |

OTHER PUBLICATIONS

Patent Abstracts of Japan, No. 178, Aug. 1984, Sankyo K.K. (The Patent Office Japanese Government).
Patent Abstracts of Japan, No. 138, Nov. 1979, Nippon Kayaku K.K. The Patent Office of Japanese Government.

*Primary Examiner*—Thurman K. Page
*Assistant Examiner*—Amy Hulina
*Attorney, Agent, or Firm*—Oblon, Spivak, McClelland, Maier & Neustadt

[57] ABSTRACT

A solid pharmaceutical sustained-release form, consisting of a core containing the active compound as well as conventional pharmaceutical auxiliaries, a coat which delays the release of the active compound and an antiadhesive outer layer, wherein the coat consists of a physiologically acceptable fat-like or wax-like hydrophobic layer which melts in the range from 30° to 120° C. and contains, in addition to conventional pharmaceutical auxiliaries, one or more water-insoluble polymers, and a process for its preparation.

2 Claims, No Drawings

SOLID PHARMACEUTICAL SUSTAINED-RELEASE FORM

The present invention relates to a solid oral drug form giving sustained release of active compound from an active compound-containing core and a coating which consists of a fat-like or wax-like hydrophobic substance which contains a water-insoluble polymer for regulating the release of active compound and, on the very outside, a lubricant (=antiadherent), and a process for the preparation of the said form.

The coating method is frequently used for the preparation of sustained-release solid forms, such as tablets, granules or pellets. For sustained-release forms, application of a diffusion-controlling coat has the advantage of virtually linear release, ie. release with zero order kinetics, equal amounts of active compound being released in each time interval.

Coating is generally carried out using coating solutions of water-insoluble polymers in organic solvents. Because of environmental pollution, toxic properties and the danger of fire, organic solvents present problems with regard to handling. When they are replaced by aqueous dispersions of these polymers, the organic solvent is absent but other disadvantages occur.

The systems are sensitive to low temperatures and microbiological contamination. Large amounts of dispersions in which the main constituent is water are expensive to handle, transport and store. Substantially larger amounts of the polymer are required, ie. about three times as much, since the homogeneity of the applied coat is poorer than in the case of organic solutions. The coating times are longer owing to the greater coat thickness, resulting in the end in a reduction in production capacity. The additives, in particular the plasticizers, have to meet higher requirements in order to ensure coalescence of the latex particles during application. The polymer costs are higher by a factor of from 2 to 6, based on the dry content of the ispersion forms, in comparison with the pure substances. These increased polymer costs in conjunction with the larger amount required and the resulting further increased coating costs make coating with aqueous dispersions seem uneconomical in spite of the saving of the organic solvents.

In order to reduce these disadvantages, the amount of the polymer would have to be decreased. However, this would lead to an inadmissible acceleration of the release of the drug.

It is an object of the present invention to overcome the problems described and to provide a simple, rapid and economical process for producing a sustained-release coat with good controllability of active compound release, which process furthermore requires very small amounts of coating.

We have found that this object is achieved by the sustained-release forms and by the process for their preparation of the invention.

The active compound-containing core may consist of a tablet, a pellet or a granule.

The term pharmaceutical sustained-release form is familiar to the skilled worker and requires no explanation.

For the purposes of the present invention, pharmaceutical active compounds are all substances having a pharmaceutical action and a very low level of side effects. The amount of active compound per unit dose may vary within wide limits depending on the activity and release rate. The only condition is that it should be sufficient to achieve the desired effect. Virtually all pharmaceutical active compounds which dissolve in the digestive tract are suitable.

Particularly suitable conventional pharmaceutical auxiliaries for the formation of the granular, tablet or pellet core are binders for the active compound, for example cellulose derivatives, polyvinylpyrrolidone or gelatine, but also, for example, inert diluents, such as dextrose, sucrose, sorbitol or mannitol.

The hydrophobic coat on the active compound-containing core should essentially consist of a physiologically acceptable fat or wax. Expressed otherwise, physiological acceptable means nontoxic. The fats are digested and the waxes are generally excreted unchanged. Examples of suitable waxes are carnauba wax, esters of montanic acid, bees' wax and cetyl palmitate. Examples of suitable fats are glycerol tristearate and glycerol tribehenate.

They are dispersed in water, in finely divided form having a mean particle diameter of 1-100 $\mu$m, not more than 10% by weight having a particle diameter of more than 100 $\mu$m.

The conventional pharmaceutical auxiliaries used for the coat may be, in particular, dispersants, such as polyvinylpyrrolidone, oxyethylated sorbitan fatty acid esters, oxyethylated hydrogenated castor oil or triglycerides of $C_8$-$C_{10}$-fatty acids, plasticizers, such as triethyl citrate, dibutyl phthalate, hydrogenated animal fat or acetylated fatty acid monoglycerides, colorants and, if required, flavorings.

According to the invention, the coats contain from 1/10 to 3, preferably from 1/5 to 2, parts, and in particular from ⅓ to 1 part, of a water-insoluble polymer per part of fat-like or wax-like hydrophobic coating material. Suitable polymers are all those conventionally used for the preparation of sustained-release coats, for example ethylcellulose, copolymers of ethyl acrylate and methyl methacrylate or of ethyl acrylate, methyl methacrylate and 2-trimethylammoniumethyl methacrylate hydrochloride.

The polymer in the hydrophobic coat has two functions: on the one hand, it acts as a binder between the fat or wax particles and between these particles and the surface of the tablet core, and on the other hand it regulates the release of active compound through the hydrophobic layer. Neither of these two functions could be foreseen.

By choosing the suitable type and amount of polymer and thickness of the hydrophobic layer, tailored in each case to the active compound, virtually any desired release rate can be obtained.

An antiadherent, such as talc, magnesium stearate or finely divided silica, is applied as the outermost layer, with an aqueous dispersion of a water-insoluble polymer, such as ethylcellulose, or an aqueous solution of a water-soluble polymer, such as methylcellulose, hydroxypropylcellulose, hydroxypropylmethylcellulose or polyvinylpyrrolidone, as the binder. The amount of anti-adherent is from 0.1 to 5%, preferably from 0.5 to 2%, based on the amount of core used. The amount of polymer of this outermost layer is from 20 to 400, preferably from 50 to 100, % by weight, based on the amount of anti-adherent.

After the coating procedure, the coated drug forms are heated to above the melting point of the hydrophobic fat-like or wax-like coating substance, ie. to a temperature of from 30° to 120° C., preferably from 40° to 100° C., in particular from 50° to 90° C.

Coating and heating are carried out in each case in the mobile state, for example in a fluidized bed apparatus, a perforated drum coater or a coating pan.

It is surprising that solid drug forms, such as tablets, granules or pellets, having a hydrophobic coating of fat-like or wax-like substances have the same linear release behavior as polymer-coated forms if the hydrophobic coat contains a water-insoluble polymer.

It is just as surprising that a fat-like or wax-like layer can be applied to solid drug forms of an aqueous, finely divided suspension of the hydrophobic substance if a water-insoluble polymer, if necessary in only small amounts, is used as a binder for the hydrophobic particles.

Although aqueous dispersions are also used in the novel process, the required amounts and hence layer thicknesses on the active compound-containing cores are small in comparison with coating only with polymers, with the result that not only is production accelerated but the cost efficiency is also increased.

EXAMPLES

1. Potassium chloride crystals in a sustained-release form

A) Composition per batch

| | |
|---|---|
| Potassium chloride crystals 0.50–1.00 mm | 3,560 g |
| Ester of montanic acid (Hoechstwachs ® E) | 140 g |
| 30% aqueous ethyl cellulose dispersion (Aquacoat ® ECD 30) dry substance | 70 g |
| Acetylated mono- and diglycerides (Myvacet ® 9-45) | 15 g |
| Monooleate of sorbitan oxyethylated with 20 units of ethylene oxide (Tween ® 80) | 1 g |
| Hyroxypropylmethylcellulose | 25 g |
| Talc | 50 g |
| Silica, finely divided | 9 g |
| | 3,870 g |

B) Preparation

The potassium chloride crystals were first coated with a suspension of the finely milled wax and 20 g of talc in the latex dispersion Aquacoat ECD 30 provided with Tween 80, the total concentration of the dispersion being 25%, in a fluidized bed coater at an inlet air temperature of 50° C. Thereafter, the antiadherent layer was applied by spraying on a suspension of the remaining talc and of the finely divided silica in a 5% strength hydroxypropylmethylcellulose solution in water. Finally, the coated crystals were heated for 30 minutes at 80° C. under fluidization.

The KCl release of the end product is strictly linear over a wide range. With 90% of the potassium chloride released after 7 h, it corresponds substantially in the release characteristics to potassium chloride coated, for comparison, with 3% of ethylcellulose from ethanolic solution. However, the novel process is simpler and more economical.

COMPARATIVE EXPERIMENT

Potassium chloride crystals coated, for comparison, with an aqueous coating of Aquacoat ECD 30 and Myvacet 9-45 (25%) with the addition of talc, having a total concentration of the dispersion of 25%, require a relative Aquacoat dry mass of 10% for comparable release of 90% after 7 h, ie. about 2.5 times the amount required according to the invention. Under optimized conditions, the coating process took about 20% longer compared with the novel process.

2. Theophylline pellets in a sustained-release form

A. Composition per batch

| | |
|---|---|
| Micronized theophylline (90% < 100 μm) | 2,625.00 g |
| Microcrystalline cellulose (Avicel ® PH 102) | 700.00 g |
| Polyvinylpyrrolidone (Kollidon ® 25) | 175.00 g |
| 30% strength aqueous dispersion of acrylate and methacrylate copolymers with trimethylammonium methacrylate (Eudragit ® RS 30 D) dry substance | 60.00 g |
| Glycerol tristearate | 100.00 g |
| Dibutyl phthalate | 15.00 g |
| (Cremophor ® RH 40) | 2.00 g |
| Methylcellulose (Methocel ® MC) | 40.00 g |
| Talc | 40.00 g |
| | 3,757.00 g |

B. Preparation

Theophylline powder was mixed with microcrystalline cellulose and polyvinylpyrrolidone in a pharmaceutical plowshare mixer and granulator, and the mixture was moistened with water. The resulting pellet-like granules were dried, and the 1–2 mm fraction was removed by sieving.

3,500 g of these pellets were first coated with a suspension of finely milled wax and 40% of the amount of talc in the latex dispersion Eudragit RS 30 provided with Cremophor RH 40, the total concentration of the dispersion being 25%, in a fluidized bed coater at an inlet air temperature of 55° C. Thereafter, the antiadherent layer was applied by spraying on a suspension of 60% of the amount of talc in a 3% strength Methocel solution in water. The coated pellets were finally heated for 30 minutes at 60° C. under fluidization.

Theophylline pellets of the same batch which had been provided with an aqueous coat of Eudragit ® RS 30 D, dibutyl phthalate (25%) and talc (30%, the percentages in each case being based on the Eudragit dry mass), having a total concentration of the dispersion of 25%, required a relative Eudragit dry mass of 6% for comparable release of 90% after 10 h, ie. 3.5 times the amount required according to the invention. Despite optimized conditions, the coating process took about 15% longer than the novel process.

I claim:

1. A solid pharmaceutical sustained-release form, comprising a core containing the active compound, a coat which delays the release of the active compound and an antiadhesive outer layer, wherein said coat comprises a physiologically acceptable fat or wax hydrophobic layer which melts in the range from 30° to 120° C. and one or more water-insoluble polymers, wherein the weight ration of the water-insoluble polymer to the fat or wax is from 1:10 to 6:10, and wherein the antiadhesive outer layer comprises 0.1 to 5 wt. %, based on the weight of the core, of an antiadherent and 20 to 40 wt. %, based on the antiadherent, of a polymer binder.

2. A process for the preparation of a solid pharmaceutical form as claimed in claim 1, wherein a mixture of an aqueous dispersion of said finely divided fat or wax and an aqueous dispersion of said water-insoluble polymer is applied to the active compound-containing cores in said defined proportions and are heated to above the melting point of the fat or wax with constant movement and are cooled again to room temperature.

* * * * *